(12) United States Patent
Terry et al.

(10) Patent No.: US 6,937,906 B2
(45) Date of Patent: Aug. 30, 2005

(54) METHOD AND APPARATUS FOR DETECTING STATIC MAGNETIC FIELDS

(75) Inventors: Michael B. Terry, Gresham, OR (US); James D. Reinke, Maple Grove, MN (US); Ron Kalin, New Hope, MN (US)

(73) Assignee: Medtronic, Inc., Minneapolis, MN (US)

( * ) Notice: Subject to any disclaimer, the term of this patent is extended or adjusted under 35 U.S.C. 154(b) by 425 days.

(21) Appl. No.: 10/059,599

(22) Filed: Jan. 29, 2002

(65) Prior Publication Data

US 2003/0144704 A1 Jul. 31, 2003

(51) Int. Cl.[7] .................................................. A61N 1/08
(52) U.S. Cl. ........................................................ 607/63
(58) Field of Search ..................................... 607/1–156

(56) References Cited

U.S. PATENT DOCUMENTS

| | | | |
|---|---|---|---|
| 4,301,804 A | 11/1981 | Thompson et al. | ... 128/419 PG |
| 5,217,010 A | 6/1993 | Tsitlik et al. | ......... 128/419 PG |
| 5,438,990 A | 8/1995 | Wahlstrand et al. | |
| 5,629,622 A | 5/1997 | Scampini | .................... 324/247 |
| 5,694,952 A | 12/1997 | Lidman et al. | |
| 5,697,958 A | 12/1997 | Paul et al. | ..................... 607/31 |
| 5,722,998 A | 3/1998 | Prutchi et al. | ................ 607/30 |
| 6,101,417 A | 8/2000 | Vogel et al. | .................. 607/30 |
| 6,209,764 B1 | 4/2001 | Hartlaub et al. | |

OTHER PUBLICATIONS

Popovic, R.S., "Not–Plate–Like Hall Magnetic Sensors and Their Applications," *Sensors and Actuators*, vol. 85, p. 9–17 (2000).

Schott et al., "Modern Integrated Silicon Hall Sensors," *Sensor Review*, vol. 18, No. 4, p. 252–57 (1998).

*Primary Examiner*—Scott M. Getzow
(74) *Attorney, Agent, or Firm*—Paul H. McDowall; Girma Wolde-Michael

(57) ABSTRACT

The present invention provides a method and apparatus for detecting magnetic fields in implantable medical devices. The apparatus includes a sensor adapted to provide at least one signal proportional to at least one vector component of a magnetic field. The apparatus further includes a circuit adapted to receive the signal and perform a predetermined action when a predetermined quantity exceeds a predetermined threshold value.

30 Claims, 7 Drawing Sheets

METHOD AND APPARATUS FOR DETECTING STATIC MAGNETIC FIELDS

FIELD OF THE INVENTION

This invention relates generally to implantable medical devices, and, more particularly, to detecting static magnetic fields in implantable medical devices.

DESCRIPTION OF THE RELATED ART

Heart pacemakers were first implanted in a human body in the 1960s. As a result of the rapid pace of innovation in both the electronic and medical fields since then, doctors now have access to a wide assortment of body-implantable electronic medical devices including pacemakers, cardioverters, defibrillators, neural stimulators, and drug administering devices, among others. Millions of patients have benefited from, and many may owe their lives to, the proven therapeutic benefits of these devices.

Implantable medical devices (IMDs) are generally adapted to be implanted near, and to deliver a therapy to, specific organs or tissues in a human body. Pacemakers, for example, may be adapted to restore normal rhythmic beating by delivering a small electric discharge to an arrhythmic heart. Drug administering devices may be adapted to provide a small dosage of a therapeutic drug to any of a variety of locations in a human body. Once implanted, an IMD may remain in the human body for many years.

Medical practitioners have long realized that it may often be beneficial to change the characteristics of the IMD without surgically removing the device. Thus, it is common practice to incorporate magnetically triggered switches in IMDs. For example, a small magnetic field may be applied to an implanted pacemaker to close a switch in the pacemaker. The closed switch may allow a battery in the pacemaker to provide power to a circuit that permits the pacemaker to receive signals from a radio-frequency transmitter. The signals from the radio-frequency transmitter may then be used to transmit a signal that may reprogram the pacemaker to alter one or more characteristics of the pacemaker, such as the amount of current delivered to the heart by the therapeutic electric discharge. In addition to reducing the likelihood of invasive surgeries to reprogram IMDs, the magnetic switches also allow the IMD to conserve limited battery power.

The IMD may, however, be exposed to magnetic fields that may disrupt its operation. For example, a doctor may find it desirable to use a magnetic resonance imaging (MRI) device to examine a patient who may have an IMD implanted within their body. Typically, the MRI device uses magnetic fields to create diagnostic images of the patient's body, or at least a portion thereof. These magnetic fields generally include a static magnetic field that typically ranges from 0.2 Tesla to 3 Tesla and two weaker pulsed magnetic fields: a gradient magnetic field and a pulsed radio-frequency magnetic field.

The magnetic fields generated by the MRI device may cause an IMD to operate unsafely. For example, the pulsed radio-frequency magnetic fields may cause components of the IMD to overheat, leading to tissue damage in the patient's body. The pulsed radio-frequency magnetic fields may also generate high electric currents in the IMD that may erroneously stimulate tissue, as well as cause sensors in the IMD to oversense and/or undersense conditions in the patient's body in such a way that may lead to the IMD providing improper therapies, thereby potentially placing the patient's health at risk. For another example, the pulsed gradient magnetic field may interfere with the IMD sensing circuitry, potentially leading the IMD to deliver improper therapies.

The present invention is directed to overcoming, or at least reducing the effects of, one or more of the problems discussed above.

SUMMARY OF THE INVENTION

In one aspect of the instant invention, an apparatus is provided for detecting magnetic fields in implantable medical devices. The apparatus includes a sensor adapted to provide at least one signal proportional to at least one vector component of a magnetic field. The apparatus further includes a circuit adapted to receive the signal and perform a predetermined action when a predetermined quantity exceeds a predetermined threshold values.

In one aspect of the present invention, a method is provided for detecting magnetic fields in implantable medical devices. The method includes sensing a magnetic field near a system using a sensor. The method further includes comparing the magnitude of the magnetic field to a predetermined threshold magnitude and notifying the system when the magnitude of the magnetic field substantially exceeds the predetermined threshold magnitude.

BRIEF DESCRIPTION OF THE DRAWINGS

The invention may be understood by reference to the following description taken in conjunction with the accompanying drawings, in which like reference numerals identify like elements, and in which.

Figure 1:
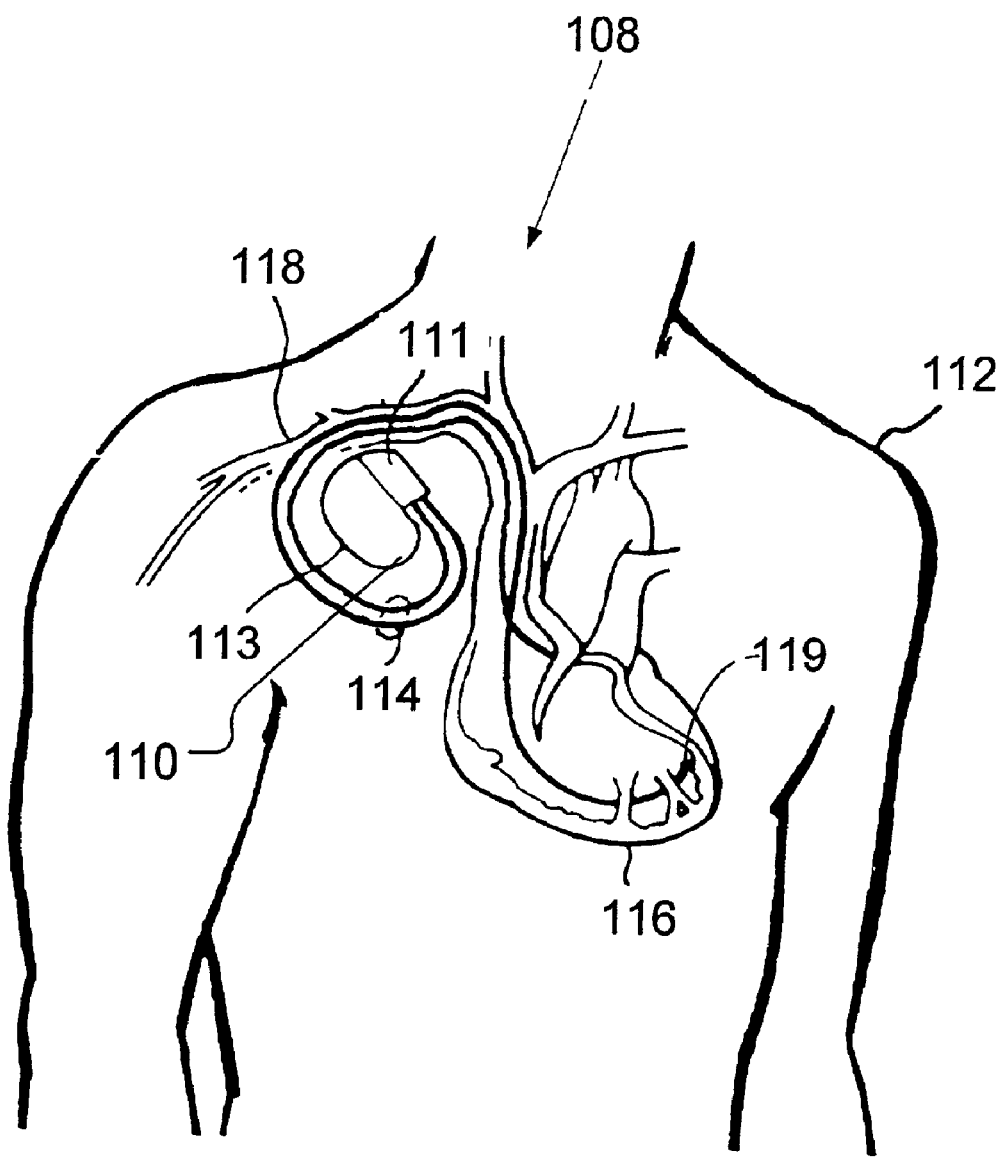
FIG. 1 schematically illustrates an implantable medical device, in accordance with one embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Referring now to FIG. 1, a stylized diagram of a system 108 in accordance with one embodiment of the present invention is shown. The system 108 comprises an implantable medical device (IMD) 110, such as an implantable cardioverter defibrillator, that has been surgically implanted in a patient 112. Although not so limited, it will be appreciated by persons of ordinary skill in the art that the IMD may also take the form of a pacemaker, a neural stimulator, or a drug administering device without departing from the spirit and scope of the present invention.

The IMD 110 may be housed within a hermetically-sealed, biologically inert casing 113. The term "hermetically-sealed," as utilized herein, should be understood to mean tightly sealed against air and liquids, in accordance with standard usage as defined by Webster's Dictionary. One or more leads, collectively identified with reference numeral 114 in FIG. 1 are electrically coupled to the IMD 110 in a conventional manner and extend into the patient's heart 116 through a vein 118. Disposed generally near an end 119 of the leads 114 are one or more exposed conductive electrodes (not shown) for receiving electrical cardiac signals or delivering electrical pacing stimuli to the heart 116. In one embodiment, the IMD 110 may administer a therapy that may reduce fibrillations in the heart 116.

The implantable medical device 110 may also collect and store physiological data from the patient 112. The physiological data may include, but need not be limited to, oxygen concentration in the blood, blood pressure, and electrocardiogram signals. Although the IMD 110 discussed in conjunction with FIG. 1 comprises a device adapted to administer therapies to the heart 116 of the patient 112, the instant invention is not so limited. In alternative embodiments, the instant invention may be used in IMDs that may be implanted in any of a variety of locations in the patient 112 and may administer any one of a variety of therapies to one or more organs or tissues in the patient 112.

The IMD 110 may be controlled by one or more processors disposed therein. Based upon the physiological data collected from the patient 112 via the one or more leads 114, the processor on the IMD 110 may determine to administer a therapy to the patient 112. For example, the physiological data may indicate to the processor that the heart 116 may be beating irregularly. Consequently, the processor may instruct the IMD 110 to deliver an electric current through the leads 114 to the heart 116. The electric current may then stimulate the heart 116 in such a way as to restore a regular rhythm to the beat of the heart 116.

Magnetic fields like those produced by magnetic resonance imaging (MRI) devices may disrupt the normal operation of the IMD 110. For example, the magnetic fields may generate currents in the IMD 110 that may cause its components to overheat, potentially leading to tissue damage in the patient 112. The magnetic fields may also cause the IMD 110 to deliver improper therapies. Thus, the processor in the IMD 110 may enter a safe mode upon detecting the presence of a magnetic field. Although not so limited, the safe mode may comprise such tasks as reducing power to components in the IMD 110 and/or turning of amplifiers that may monitor signals from leads 114. Hereinafter, magnetic fields that may disrupt the normal operation of the IMD 110, like those that may be found in MRI devices, will be referred to as "MRI fields." Although not so limited, MRI fields may include a static magnetic field ranging from 0.2 Tesla to 3 Tesla, a pulsed gradient magnetic field, and a pulsed radio-frequency magnetic field. However, it should be noted that this term is not limited to magnetic fields found in MRI devices, and may refer to magnetic fields that may be found in any one of a variety of environments.

Although magnetic fields like those produced by MRI devices may be disruptive to the operation of the IMD 110, it is important to note that not all magnetic fields that may be applied to the IMD 110 are disruptive. For example, a small magnetic field may be applied to the IMD 110 as a step in a method of non-invasively programming the IMD 110. Magnetic fields that generally do not disrupt the normal operation of the IMD 110, like those that may be used to program the IMD 110, will hereinafter be referred to as "probe fields." However, it will be appreciated that the aforementioned term will not be limited to magnetic fields used for programming the IMD 110, but may include magnetic fields that may be found in a variety of environments.

To better distinguish between non-disruptive probe fields and potentially disruptive MRI fields, the IMD 110 may be adapted to detect static magnetic fields above a certain magnetic field strength threshold, such as those that may generally be found in or near an MRI device. As will be discussed in more detail below, and in accordance with the present invention, the IMD 110 includes a three-dimensional Hall detector that may enable the IMD 110 to reliably detect the static magnetic field that may indicate the presence of disruptive MRI fields. The IMD 110 may further include one or more devices adapted to use the signals produced by the 3-D Hall detector to notify the processor that it may be desirable to enter the safe mode. By instructing the IMD 110 to enter the safe mode when the IMD 110 may be exposed to magnetic fields like those found in MRI devices, the 3-D Hall effect detector may allow the IMD 110 to reduce tissue damage to the patient 112, as well as reduce the probability of administering inappropriate therapies to the patient 112.

Figure 2:
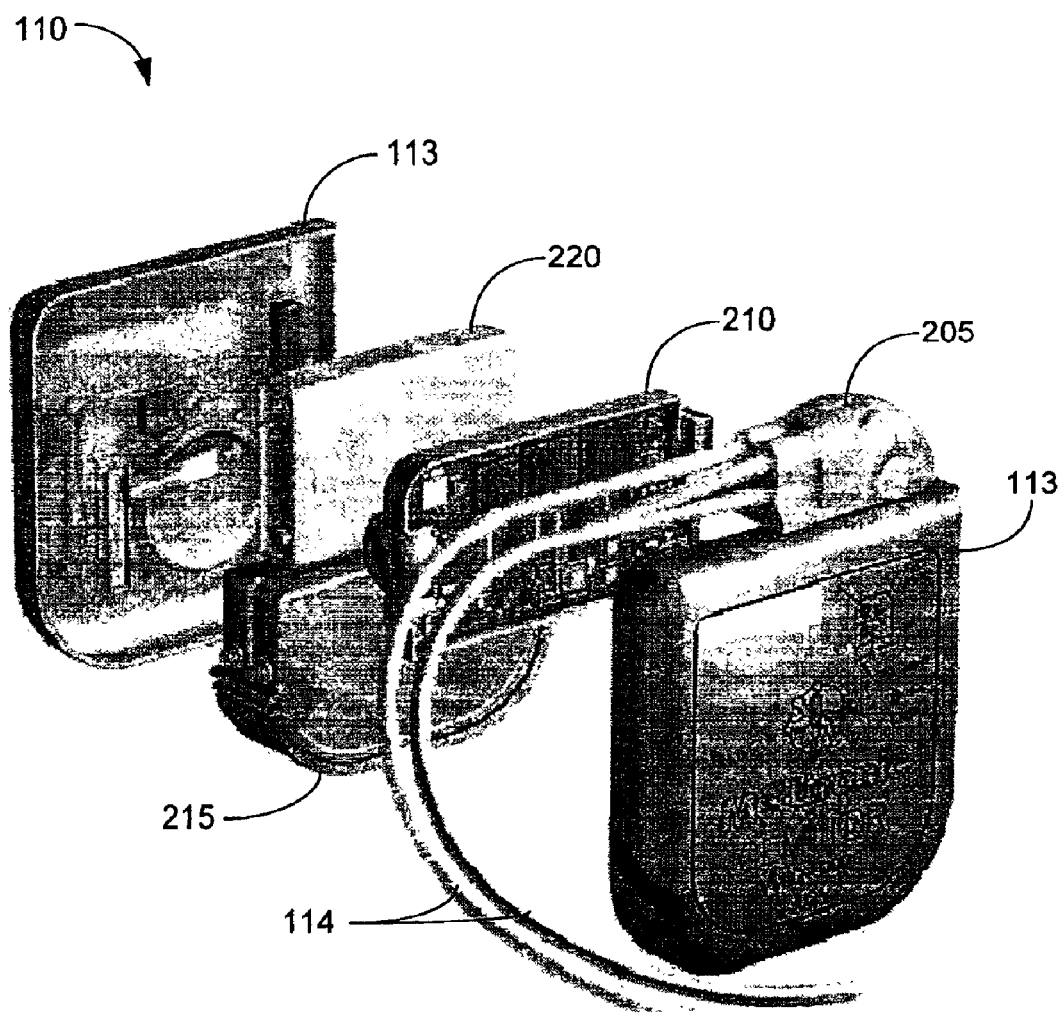
FIG. 2 shows a three-dimensional exploded view of an implantable medical device that may be employed in the system of FIG. 1, according to one embodiment of the present invention.

Turning now to FIG. 2, a stylized three-dimensional depiction of one embodiment of the IMD 110 is illustrated. In one embodiment, the casing 113 may include a variety of elements including, but not necessarily limited to, a connector 205, a processor unit 210, a capacitor package 215, and a battery 220 that may provide power to the IMD 110. The elements in the casing 113 may be positioned in any of a variety of locations. The capacitor package 215 and the battery 220 may be electrically coupled to the processor unit 210. The leads 114 may be interfaced with the implantable medical device 110 through the connector 205 and may electrically connect tissues and/or internal organs of the patient 112, such as the heart 116, to the implantable medical device 110.

The processor unit 210 may detect and/or record electric cardiac signals that travel from the heart 116 along the leads 114 and enter the implantable medical device 110 through the connector 205. The processor unit 210 may use the electric cardiac signals to determine when a cardiac event, such as a slow or erratic heart rate, occurs. In response to such a cardiac event or other conditions, the processor unit 210 may administer electric pacing stimuli to the heart 116 by releasing energy stored in the capacitor package 215 and directing the energy through the leads 114 to the heart 116. The capacitor package 215 may include one or more capacitors (not shown) that may store sufficient charge, such that when the charge is released, it may provide a cardiac therapy.

Figure 3:
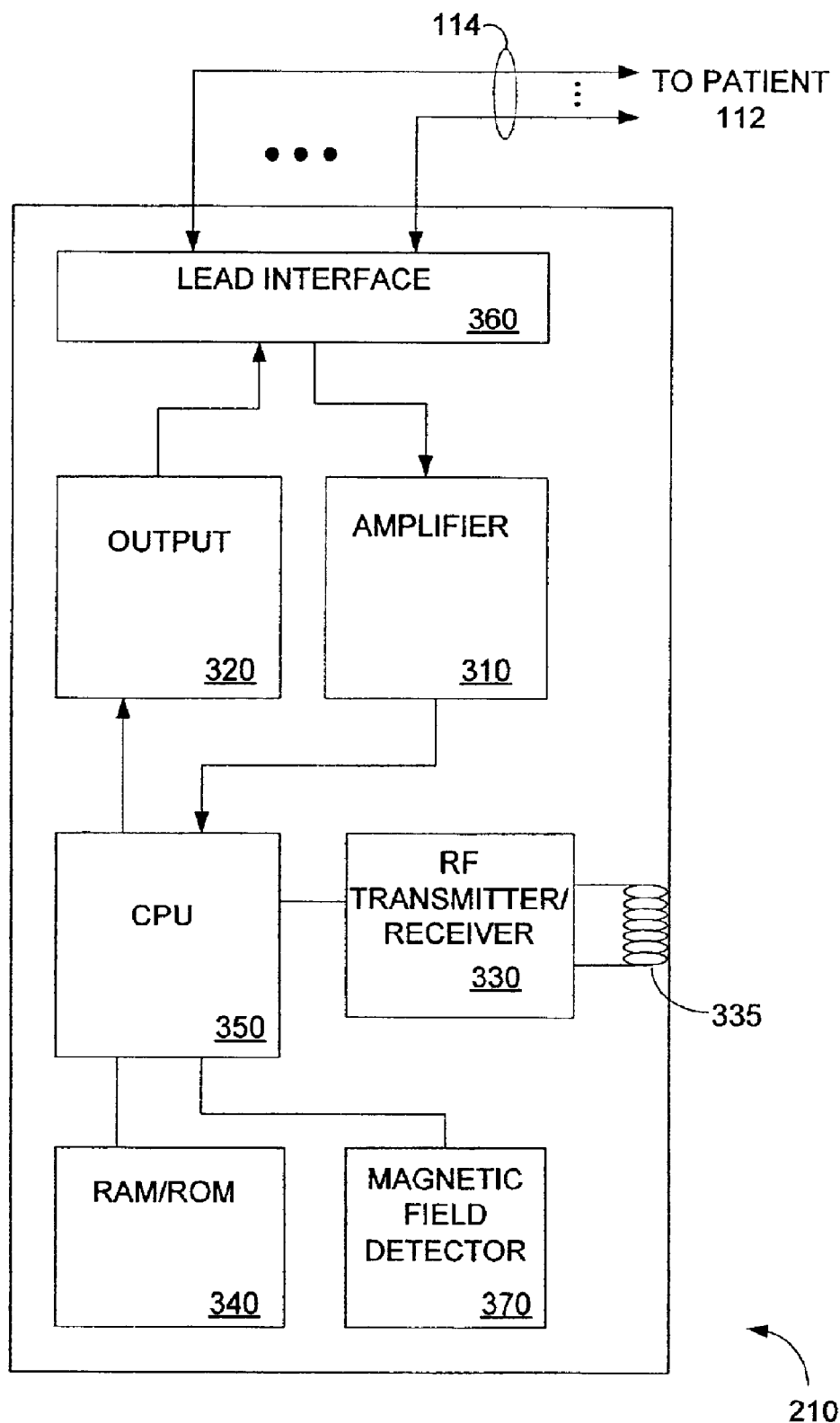
FIG. 3 depicts a stylized block diagram of a processing unit that may be used in the implantable medical device illustrated in FIG. 2, in accordance with one embodiment of the present invention.

Referring now to FIG. 3, a stylized block diagram of the processor unit 210 that may be used in the IMD 110 is illustrated, in accordance with one embodiment of the present invention. Although not so limited, the processor unit 210 may include such components as an amplifier 310, an output 320, a transmitter/receiver 330 coupled to an antenna 335, a random-access memory and read-only memory (RAM/ROM) unit 340, a central processing unit (CPU) 350, and a lead interface 360, which functions, in a multiplexer-like manner, to establish necessary connections between the leads 114 and individual electrical components of the processor unit 210. However, it will be appreciated that additional components, such as clocks and I/O devices which are not shown in FIG. 3, may be included in the processing unit 210 without departing from the spirit or scope of the instant invention.

According to one embodiment, the CPU 350 may be adapted to receive physiological data over the leads 114. The data transmitted by the leads 114 may take the form of electric currents or voltages that may be amplified by the amplifier 310 before being transmitted to the CPU 350. In one embodiment, the CPU 350, acting under control of software stored in the RAM/ROM unit 340, may collect and store the physiological data in the RAM/ROM unit 340. The CPU 350 may use the physiological data to determine when it may be desirable to provide a therapy to the patient 112 through the output 320. For example, data indicating the timing of recent heartbeats may be used to detect an arrhythmic heart beat, in which case the CPU 350 may direct the output 320 to provide an electric discharge that may be transmitted through the lead interface 360 to the heart via the leads 114.

Occasionally, it may be desirable to non-invasively program the CPU 350. For example, a doctor may determine that a smaller or larger electrical discharge may provide a more effective therapy to treat heart arrhythmia in the patient 112. In one embodiment, the transmitter/receiver 330 may be adapted to receive radio-frequency (RF) signals through the antenna 335. The RF signals may be used to non-invasively program the CPU 350. However, because the transmitter/receiver 330 may not be used frequently, the power consumed by the receiver 350 may be limited by turning off the receiver 350 when it is not receiving signals. According to one embodiment, the power supplied to the receiver 350 may be restored to enable non-invasive programming by applying a probe field to close a switch (not shown) in the receiver 350.

The amplifier 310 may also be exposed to MRI fields that may disrupt its operation. For example, in one embodiment, MRI fields such as the pulsed radio-frequency magnetic field may create electric currents that may that may be transmitted to the amplifier 310. This may cause the CPU 350 to misinterpret the information received from the amplifier 310, and cause the output to deliver inappropriate electrical stimuli to the patient 112 through the leads 114, which may damage tissue in the patient 112. Thus, in one embodiment, the processor unit 210 may further comprise a magnetic field detector 370, which may be adapted to detect both the probe fields, such as those used to turn on the transmitter/receiver 330, and the static magnetic field that may indicate the presence of disruptive MRI fields such as the pulsed gradient magnetic field and the pulsed radio-frequency magnetic field. In the event that the magnetic field detector 370 detects the presence of the static magnetic field, the magnetic field detector 370 may be adapted to instruct the CPU 350 to enter into the safe mode of operation.

Figure 4A:
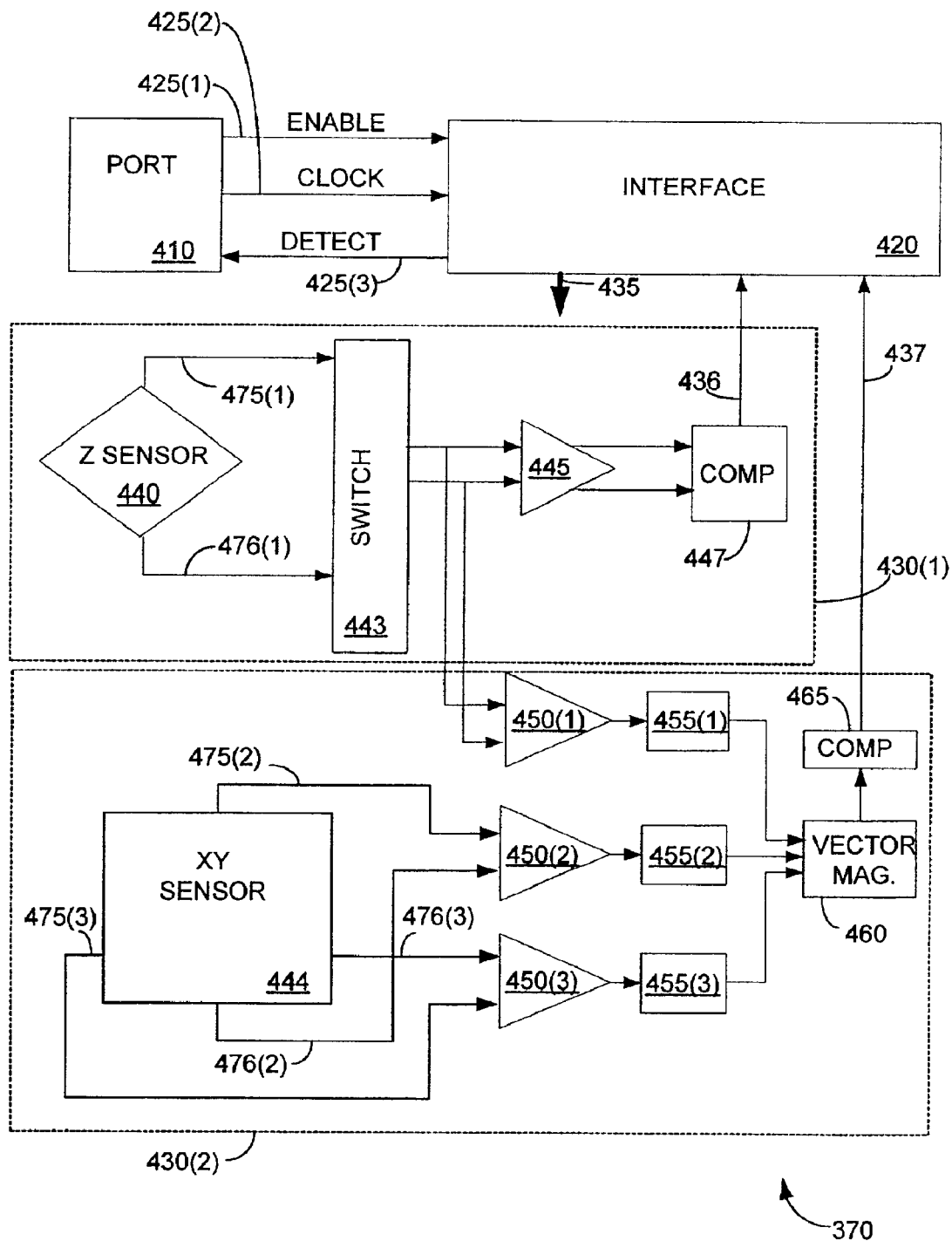
FIGS. 4A–B show a stylized block diagram of a magnetic field detector that may be employed in the processing unit depicted in FIG. 3, in accordance with one embodiment of the present invention.

Turning now to FIG. 4A, a more detailed block diagram of a magnetic field detector 370 is provided according to one embodiment of the present invention. The magnetic field detector 370 may comprise a port 410 that may be adapted to notify the CPU 350 in the event that the static magnetic field that may indicate the presence of a potentially disruptive MRI field has been detected. The port 410 may, in one embodiment, further be coupled to an interface 420 through one or more connections 425(1–3). In one embodiment, an enable line 425(1), a clock line 425(2), and a detect line 425(3) may carry signals between the port 410 and the interface 420. It should be appreciated, however, that in alternative embodiments signals may be transmitted between the port 410 and the interface 420 along any number of connections 425(1–3) without departing from the spirit and scope of the present invention.

The interface 420 may, in one embodiment, be coupled to two detection circuits 430(1–2). However, it will be appreciated that, in alternative embodiments, the magnetic field detector 370 may include more or fewer detection circuits 430(1–2) without departing from the spirit and scope of the present invention. In the interest of clarity, the specific connections by which the interface 420 may be coupled to the detection circuits 430(1–2) have been represented in FIG. 4 by a single arrow 435, although it will be appreciated by those of ordinary skill in the art that, for example, the interface 420 may provide power to each element of the detection circuits 430(1–2), as well as other signals (described in detail below) that may be used by the detection circuits 430(1–2). The interface 420 may also be adapted to receive signals from the detection circuits 430(1–2) along the magnet detect line 436 and the MRI detect line 437.

The detection circuit 430(1) may, in one embodiment, comprise a Z-field sensor 440 coupled to a switch 443. The Z-field sensor 440 may be adapted to detect magnetic fields aligned perpendicular to the plane of the Z-field sensor 440. The detection circuit 430(2) may comprise an XY-field sensor 444 adapted to detect magnetic fields aligned in the two orthogonal directions oriented approximately in the plane of the Z-field sensor 440. When combined, the Z-field sensor 440 and the XY-field sensor 444 may, in one embodiment, be adapted to measure the strength of the three orthogonal vector components of a magnetic field with an arbitrary orientation. Accordingly, in one embodiment, the Z-field sensor 440 and the XY-field sensor 444 may be used to measure the magnitude of a magnetic field with an arbitrary orientation.

Figure 4B:
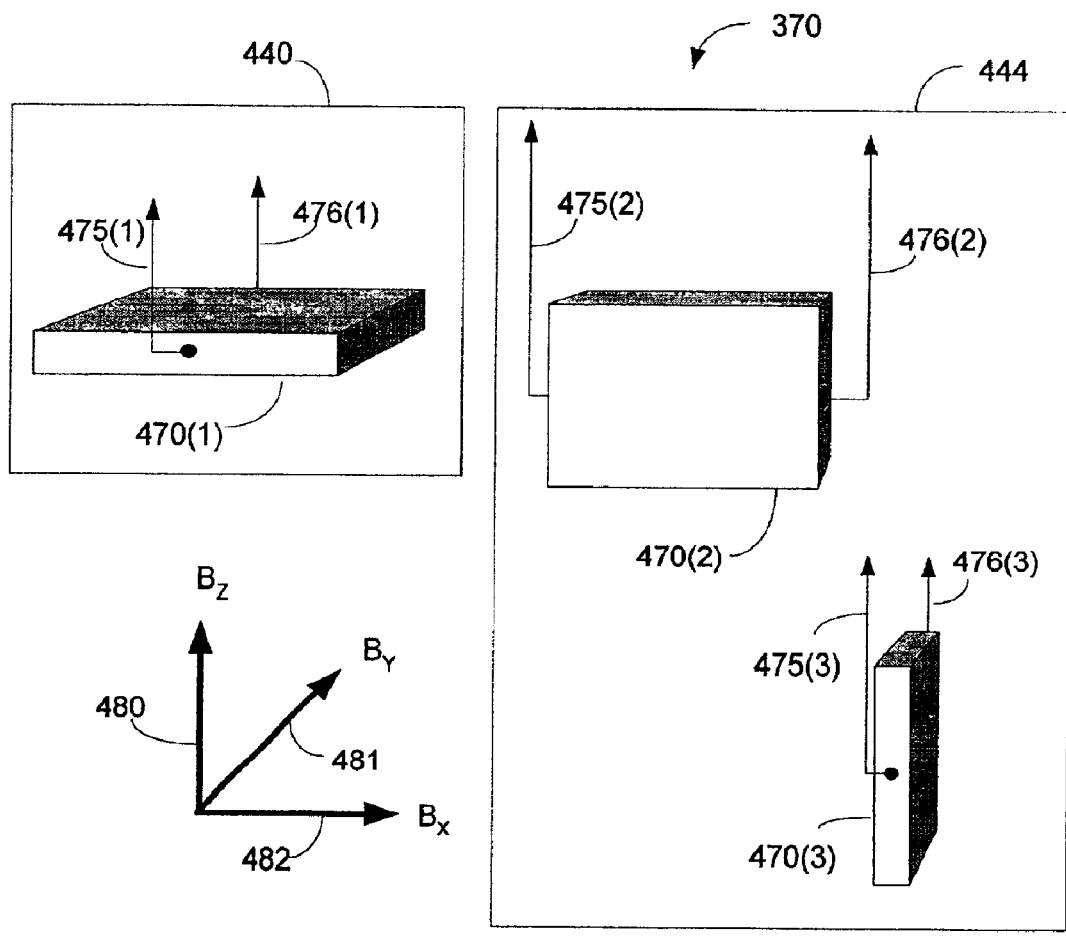

Referring now to FIG. 4B, a stylized diagram of the Z-field sensor 440 and the XY-field sensor 444 that may be used in the magnetic field detector 370 is shown. In one embodiment, the Z-field sensor 440 and the XY-field sensor 444 may be formed by methods well known to those of ordinary skill in the art. For example, one or more horizontal Hall detectors 470(1–3) may be formed in a semiconducting silicon substrate. The horizontal Hall detectors 470(1–3) may, in one embodiment, be adapted to provide a voltage through the lines 475(1–3) and 476(1–3) that may be approximately proportional to a component of the magnetic field oriented perpendicular to the plane of the horizontal Hall detectors 470(1–3).

The Z-field sensor 440 may, in one embodiment, be formed of a single horizontal Hall detector 470(1) oriented perpendicular to one component of the magnetic field indicated by the arrow 480 (hereinafter referred to as $B_Z$). The XY-field sensor 444 may, in one embodiment, be formed by a pair of horizontal Hall detectors 470(2–3) oriented orthogonal to each other and to the Z-field sensor 440. In one embodiment, the horizontal Hall detector 470(2) may be adapted to detect a component of the magnetic field directed perpendicular to the plane of the horizontal Hall detector 470(2), indicated by an arrow 481 (hereinafter referred to as $B_Y$). The horizontal Hall detector 470(3) may then be adapted to detect a component of the magnetic field directed perpendicular to the plane of the horizontal Hall detector 470(3), indicated by an arrow 482 (hereinafter referred to as $B_X$).

Referring back to FIG. 4A, the switch 443 in the detection circuit 430(1) may be adapted to receive signals from the Z-field sensor 440. The signals may, in one embodiment, comprise a voltage related to the strength of the component of the magnetic field directed approximately perpendicular to the Z-field sensor 440. The switch 443 may transmit the voltage to an amplifier 445, which may amplify the voltage and transmit the amplified voltage to a voltage comparator 447. If the voltage signal substantially exceeds a predetermined threshold voltage, the voltage comparator 447 may transmit a logic high signal to the interface 420. For example, in one embodiment, the voltage comparator 447 may transmit a logic high signal to the interface 420 when the Z-field sensor 440 is exposed to a $B_Z$ of 15 Gauss. In an alternative embodiment, the logic high signal may be transmitted to the interface 420 when the Z-field sensor 440 may be exposed to either a probe field or an MRI field.

In one embodiment, the switch 443 in the detection circuit 430(1) may also provide a voltage roughly proportional to $B_Z$ to an amplifier 450(1) in the circuit 430(2). As discussed above, the XY-field sensor 444 in the detection circuit 430(2) may produce two voltages that may be approximately proportional to $B_X$ and $B_Y$. The two voltages may, in one embodiment, be transmitted to amplifiers 450(2–3), which may convert the voltages to currents $I_X$, $I_Y$, and $I_Z$ that are approximately proportional to $B_X$, $B_Y$, and $B_Z$.

The voltages produced by the Z-field sensor 440 and the XY-field sensor 444 may be positive or negative, depending on the orientations of $B_X$, $B_Y$, and $B_Z$. Thus, the amplifiers 450(1–3) may produce either positive or negative currents $I_X$, $I_Y$, and $I_Z$. In an alternative embodiment, positive currents may be provided and so the currents $I_X$, $I_Y$, and $I_Z$ may be transmitted from the amplifiers 450(1–3) to absolute value circuits 455(1–3) that may produce an absolute value of the currents $|I_X|$, $|I_Y|$, and $|I_Z|$. In one embodiment, the absolute value circuits 455(1–3) may be translinear circuits comprising one or more bipolar transistors (not shown). In an alternative embodiment, however, the absolute value circuits 455(1–3) may be formed by any one of a variety of means, well established in the art, without departing from the spirit and scope of the instant invention.

To convert the currents $|I_X|$, $|I_Y|$, and $|I_Z|$ into a single current that may be approximately proportional to the magnitude of the magnetic field, the currents $|I_X|$, $|I_Y|$, and $|I_Z|$ may be transmitted to a vector magnitude circuit 460. In one embodiment, the vector magnitude circuit 460 may be a translinear circuit, which is well known to those of ordinary skill in the art, comprising one or more bipolar transistors (not shown). The vector magnitude circuit 460 may be adapted to transmit a voltage $V_M$ that may be proportional to the vector magnitude of the currents $|I_X|$, $|I_Y|$, and $|I_Z|$, which may be defined as $$V_M \propto \sqrt{|I_X|^2 + |I_Y|^2 + |I_Z|^2}.$$

The vector magnitude circuit 460 may transmit the voltage $V_M$ to a voltage comparator 465. If the voltage signal substantially exceeds a threshold voltage corresponding approximately to a static MRI magnetic field, the voltage comparator 465 may transmit a logic high signal to the interface 420 via signal line 437. For example, the voltage comparator 465 may transmit a logic high signal to the interface 420 when the magnetic field detector 370 is exposed to a 1700 Gauss magnetic field.

In accordance with the illustrated embodiment, the detection circuits 430(1–2) may draw their power from the battery 220 (as illustrated in FIG. 2). As a result, the power drawn by the detection circuits 430(1–2) may undesirably reduce the effective lifetime of the battery 220, thereby reducing the amount of time the IMD 110 may remain implanted within the patient 112.

Figure 5:
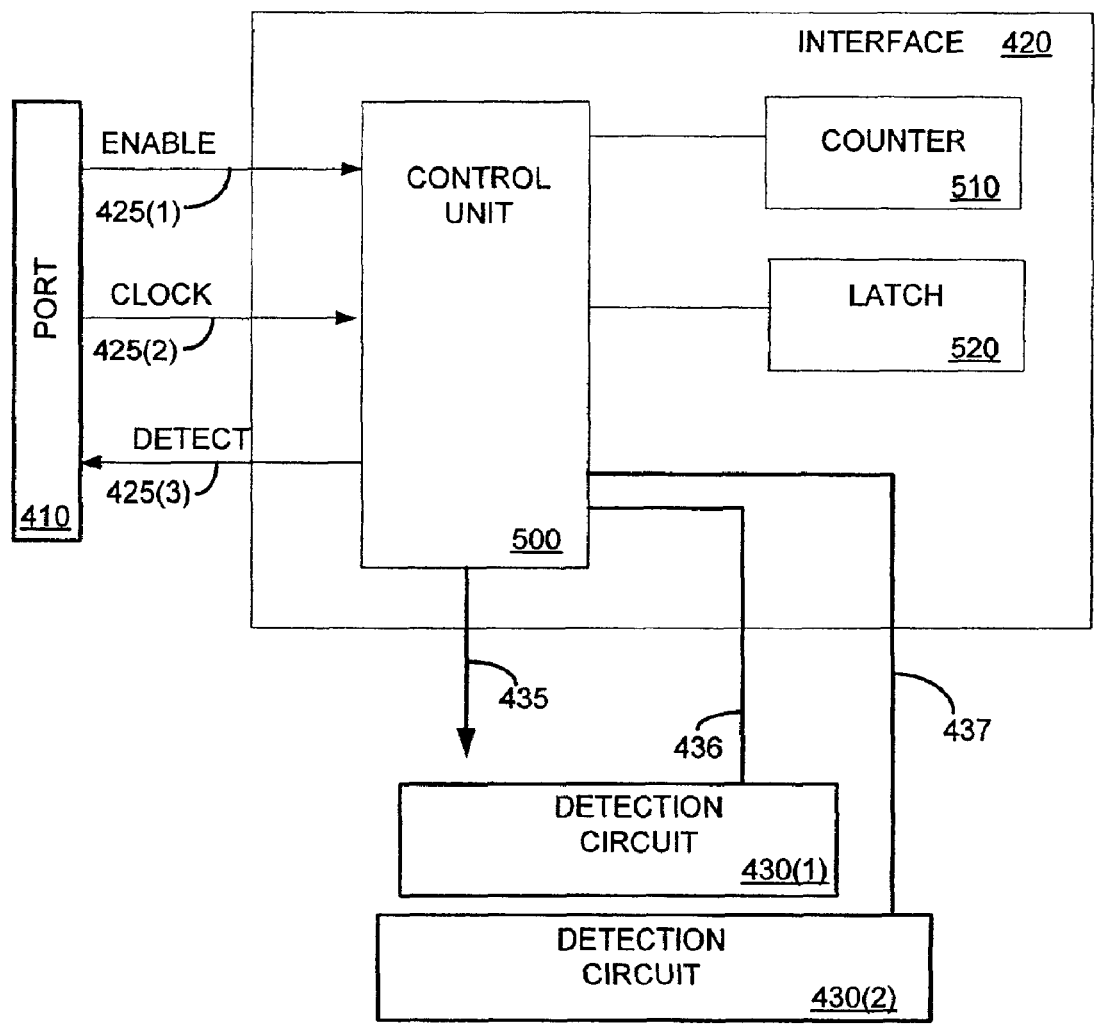
FIG. 5 shows a stylized block diagram of an interface that may be used in the magnetic field detector shown in FIGS. 4A–B, in accordance with one embodiment of the present invention.

FIG. 5 shows a stylized block diagram illustrating the interface 420 that may be used to manage power supplied to the detection circuits 430(1–2). As will be discussed in more detail below, in one embodiment, the interface 420 may comprise a control unit 500 that may be coupled to a counter 510 and a latch 520. The control unit 500 of the interface 420 may be coupled to the port 410 along the enable line 425(1), the clock line 425(2), and the detect line 425(3). The control unit 500 may also coupled to the detection circuits 430(1–2) by the magnet detect line 436 and the MRI detect line 437, as well as by the line 435.

Figure 6:
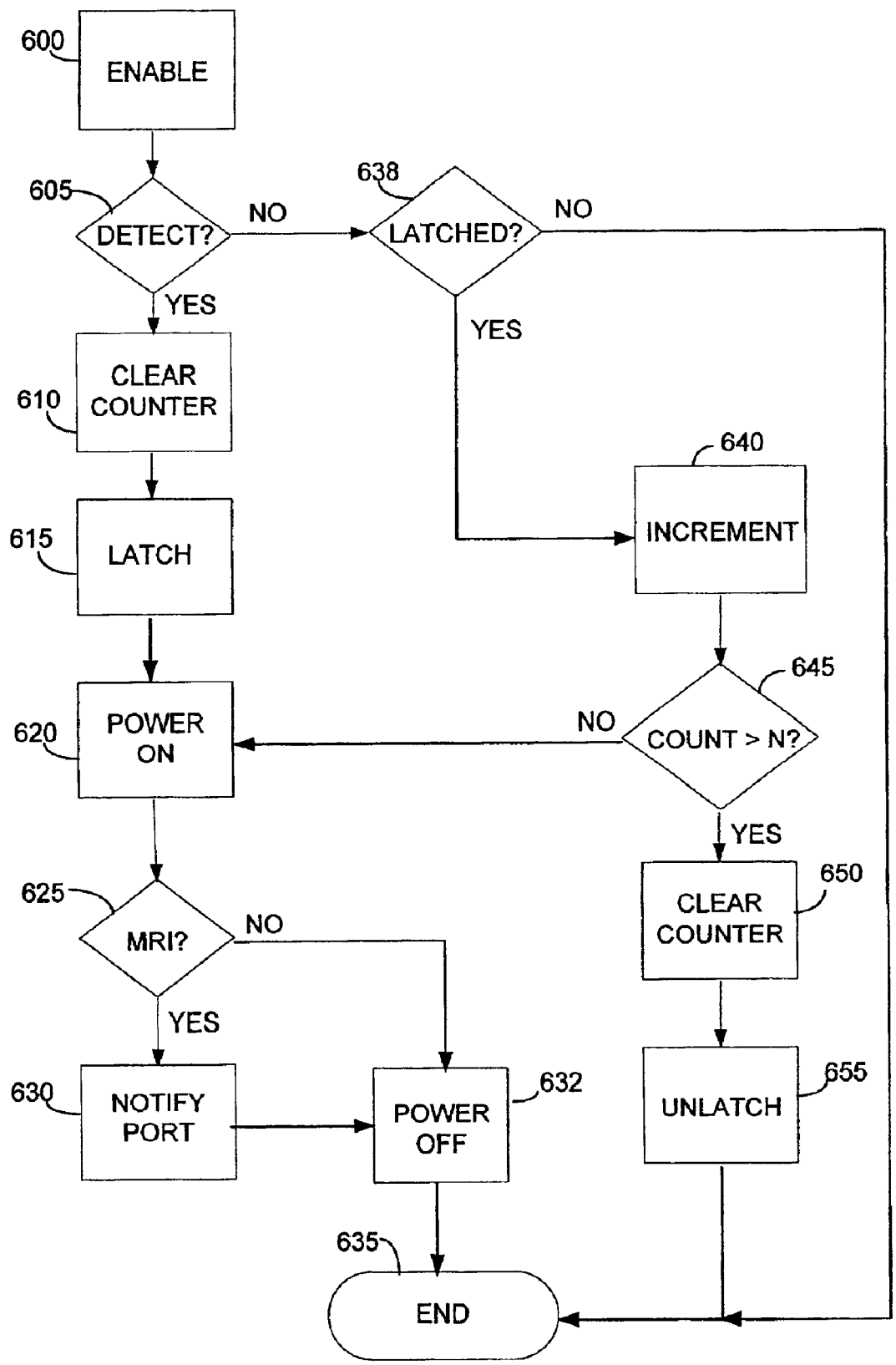
FIG. 6 shows a flow diagram that illustrates a method that may be used by the magnetic field detector shown in FIGS. 4A–B, in accordance with one embodiment of the present invention.

FIG. 6 shows a flow diagram illustrating one method by which the interface 420 may manage the power that may be supplied to the magnetic field detector 370, in accordance with one embodiment of the present invention. The port 410 may periodically enable (at 600) a magnet detection cycle by sending a logic high signal through the enable line 425(1) to the control unit 500 in the interface 420. For example, in one embodiment, the port 410 may enable (at 600) the control unit 500 approximately once per second. The control unit 500 may then examine (at 605) the signal from the comparator 447 that may be transmitted from the detection circuit 430(1) along the magnet detect line 436. If the signal is logic high, indicating that the Z-field sensor 440 may have detected a magnetic field, the control unit 500 may clear (at 610) the counter 510. As will be discussed in more detail below, the counter 510 may be adapted to count consecutive magnet non-detections. The control unit 500 may then set (at 615) the latch 520 to indicate that a magnetic field has been detected and turn on (at 620) the power to the detection circuit 430(2).

The Z-field sensor 440 in the detection circuit 430(1) and the XY-field sensor 444 in the detection circuit 430(2) may then be used, in one embodiment, to approximately measure the magnitude of the magnetic field. If the magnitude of the magnetic field substantially exceeds (at 625) a threshold value for a static MRI magnetic field, e.g. 1700 Gauss, the control unit 500 in the interface 420 may notify (at 630) the port 410 by returning (at 635) a logic high signal to the port 410 through the line 425(3). The interface 420 may then power off (at 632) the detection circuit 430(2) and end (at 635) the magnet detection cycle. If the magnitude of the magnetic field does not substantially exceed (at 625) a threshold value for a static MRI magnetic field, e.g. 1700 Gauss, the control unit 500 in the interface 420 may power off (at 632) the detection circuit 430(2) and end (at 635) the magnet detection cycle by sending a logic low signal to the port 410.

If a magnetic field is not detected (at 605), it may not necessarily indicate that no magnetic field is present. For example, the Z-field sensor 440 may not be sensitive to magnetic fields that may be oriented parallel to the plane of the Z-field sensor 440 and thus the Z-field sensor 440 may erroneously return a logic low signal along the line 436 to the control unit 500 in the interface 420, indicating that no magnetic field has been detected. To reduce the probability that an erroneous logic low may be transmitted to the control unit 500, the control unit 500 may, in one embodiment, examine (at 638) the latch 520. If the latch 520 is not set, indicating that a magnetic field has not been detected in a selected number of previous magnet detection cycles, the control unit 500 may then, in one embodiment, return (at 635) a logic low signal to the port 410 along the detect line 425(3), ending the magnet detection cycle.

If the control unit 500 in the interface 420 determines (at 638) that the latch 520 may be set, the control unit 500 may increment (at 640) the counter 510 that may, in one embodiment, count the number of magnet detection cycles that may have been substantially completed since the last detection (at 605) of a magnetic field by the detection circuit 430(1). If the control unit 500 of the interface 420 determines (at 645) that the value of the counter 510 may be less that a predetermined number, N, indicating that a magnetic field may have been detected during a recent magnet detection cycle, the interface 420 may, in one embodiment, initiate (at 620) the MRI detect sequence. For example, in one embodiment, once a magnetic field may be detected (at 605), the interface 420 may continue to check (at 625) for the presence of the static MRI field for a predetermined value of N=8 magnet detection cycles after the detection (at 605).

The control unit 500 may, however, determine (at 645) that the counter 510 has substantially exceeded the predetermined value of N, indicating that no magnetic field has been detected (at 605) in approximately N magnet detection cycles. The control unit 500 may then, in one embodiment, clear (at 650) the counter 510, unset (at 655) the latch 520, turn off (at 660) power to the detection circuit 430(2), and return (at 635) control to the port 410, ending the magnet detection cycle. By turning off (at 660) power to the detection circuit 430(2), the control unit 500 may conserve the limited power of the battery 220 and, accordingly, may substantially prolong the operational life of the IMD 110.

The method described above may substantially reduce the probability that magnetic fields like those that may be found in MRI devices may cause the IMD 110 to malfunction and potentially harm the patient 112. When notified (at 630) of the possible presence of magnetic fields like those that may be encountered in an MRI device, the port 410 may, in one embodiment, instruct the IMD 110 to enter a safe mode that may substantially reduce the chance that the IMD 110 may malfunction. For example, the safe mode may comprise measures adapted to reduce the high electric currents that may be generated in the IMD 110 by magnetic fields and that may erroneously stimulate tissue, as well as causing sensors in the IMD 110 to oversense and/or undersense conditions in the patient's body in such a way that may lead to the IMD 110 providing improper therapies. Although not so limited, the safe mode may comprise such tasks as reducing power to components in the IMD 110 and/or turning off amplifiers that may monitor signals from leads 114. For patients with low or no intrinsic heart rhythm, the safe mode may provide pacing therapy at a predetermined lower rate.

The IMD 110 may leave the safe mode once the magnetic fields are no longer detected. For example, when patient 112 leaves the MRI room, the magnetic field detector 370 may instruct the CPU 350 to turn off the safe mode and revert to normal operation. The IMD 110 may also provide diagnostic information with a time stamp to indicate when the presence of a high magnetic field was detected. This diagnostic information may aid the health professional in determining if the MRI scan affected the sensing or stimulation thresholds, or if other environments the patient 112 encountered in their daily life exposed them to a high magnetic field.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. An apparatus for detecting static magnetic fields impinging upon an implantable medical device (IMD), comprising:

a sensor adapted to provide at least one signal proportional to at least one vector component of a magnetic field;

a circuit adapted to receive the signal and perform a predetermined action when a predetermined quantity exceeds a predetermined threshold value, wherein the at least one signal comprises a first, a second, and a third signal approximately proportional to a first, a second, and a third vector component of the magnetic field, wherein the second and the third components of the magnetic field are approximately orthogonal to the first component of the magnetic field and to each other, and wherein the circuit comprises a first detection circuit and a second detection circuit coupled to an interface and wherein said circuit operatively couples to control circuitry of an IMD.

2. The apparatus of claim 1, wherein the sensor comprises a first Hall detector adapted to provide the first signal.

3. The apparatus of claim 2, wherein the sensor further comprises a second and a third Hall detector adapted to provide the second and the third signal.

4. The apparatus of claim 1, wherein at least one of the first, the second, and the third signals is a voltage.

5. The apparatus of claim 1, wherein at least one of the first, the second, and the third signals is a current.

6. The apparatus of claim 1, wherein the first detection circuit comprises a first comparator adapted to receive the first signal from the sensor and transmit a first notification to the interface if the signal substantially exceeds a first predetermined value.

7. The apparatus of claim 6, wherein the first predetermined value is approximately equal to the signal produced in the first detection circuit by a magnetic field of about 15 Gauss.

8. The apparatus of claim 7, wherein the second detection circuit comprises a vector magnitude circuit adapted to compute the predetermined quantity.

9. The apparatus of claim 8, wherein the predetermined quantity is a vector magnitude computed from the first, the second, and the third signals.

10. The apparatus of claim 9, wherein the second detection circuit further comprises a second comparator adapted to receive the vector magnitude and transmit a second notification to the interface if the vector magnitude substantially exceeds the predetermined threshold value.

11. The apparatus of claim 10, wherein the predetermined threshold value is approximately equal to the vector magnitude produced by a magnetic field with a magnitude of about 1700 Gauss.

12. The apparatus of claim 11, wherein the predetermined action comprises a third notification transmitted from the interface to a port in response to the second notification that the vector magnitude substantially exceeds the predetermined threshold value.

13. The apparatus of claim 6, wherein the interface is adapted to manage power supplied to the second detection circuit using the first notification from the first detection circuit.

14. The apparatus of claim 1, wherein the apparatus comprises an IMD selected from the group: a pacemaker, an implantable cardioverter-defibrillator, a neural stimulator, a drug administering device.

15. An apparatus for detecting static magnetic fields impinging upon an implantable medical device (IMD), comprising:
a first detection circuit adapted to receive a first portion of a signal provided by a sensor positioned in an implantable medical device, wherein the sensor is adapted to sense the presence of a magnetic resonance imaging device;
a second detection circuit adapted to receive at least a second portion of the signal; and
an interface adapted to receive a first notification from the first detection circuit when a first selected quantity derived from the first portion exceeds a first selected value and a second notification from the second detection circuit when a second selected quantity derived from the second portion substantially exceeds a second selected value, and wherein the interface is adapted notify a processor unit operatively coupled within the interior portion of a hermetically-sealed IMD when the second selected quantity substantially exceeds the second selected value, wherein the interface as adapted to provide power to the second detection circuit following the first notification from the first detection circuit that the first selected quantity substantially exceeds the first selected value.

16. The apparatus of claim 15, wherein the signal comprises a first, a second, and a third voltage proportional to a first, a second, and a third vector component of a magnetic field produced by the magnetic resonance imaging device.

17. The apparatus of claim 16, wherein the sensor comprises a first, a second, and a third Hall detector adapted to provide the first, the second, and the third voltage.

18. The apparatus of claim 17, wherein the second detection circuit comprises three amplifiers adapted to receive the first, the second, and the third voltages and convert them into a first, a second, and a third current.

19. The apparatus of claim 18, wherein the second detection circuit further comprises a vector magnitude circuit adapted to compute a vector magnitude of the first, the second, and the third voltages.

20. The apparatus of claim 19, wherein the second selected quantity is the vector magnitude.

21. The apparatus of claim 20, wherein the second selected value is approximately equal to the vector magnitude produced in the second detection circuit by a magnetic field of approximately 1700 gauss.

22. A method of detecting static magnetic fields impinging upon an implantable medical device (IMD), comprising:
sensing a magnetic field impinging upon an IMD system using a sensor;
comparing the magnitude of the magnetic field to a predetermined threshold magnitude;
notifying the IMD system when the magnitude of the magnetic field substantially exceeds the predetermined threshold magnitude,
wherein sensing the magnetic field comprises forming three signals proportional to a first, a second, and a third vector components of the magnetic field, wherein the second and the third components of the magnetic field are approximately orthogonal to the first component of the magnetic field and to each other,
wherein comparing the magnitude of the magnetic field comprises combining the three signals using a circuit to form a quantity approximately proportional to the magnitude of the magnetic field,
wherein comparing further comprises determining if the quantity substantially exceeds a value that would be created in the circuit by a magnetic field with a magnitude approximately equal to the predetermined threshold magnitude, and
wherein comparing comprises determining if the quantity substantially exceeds the value that would be created in the circuit by a magnetic field of approximately 1700 gauss.

23. The method of claim 22, wherein forming three signals comprises forming three voltages.

24. The method of claim 22, wherein forming three signals comprises forming three currents.

25. The method of claim 22, wherein sensing the magnetic field comprises using a three-dimensional Hall detector.

26. A method of detecting static magnetic fields impinging upon an implantable medical device (IMD), comprising:
sensing a first, a second, and a third signal proportional to a first, a second, and a third component of a magnetic field near an IMD using a three-axis sensor, the second and the third components of the magnetic field being approximately orthogonal to the first component of the magnetic field and to each other;
deriving a first quantity from the first signal;
comparing the first quantity to a first selected value using a first detection circuit;
comparing a second quantity derived from the first, the second, and the third signal to a second selected value using a second detection circuit, the second detection circuit being enabled following notification that the first quantity substantially exceeds the first selected value; and
notifying a processing unit in the IMD when the second quantity substantially exceeds the second selected value.

27. The method of claim 26, wherein comparing the first quantity to the first selected value comprises comparing the first quantity to the value of the first quantity that would be produced in the first detection circuit by a magnetic field of greater than 17 gauss.

28. The method of claim 26, wherein enabling the second detection circuit comprises supplying power to the second detection circuit.

29. The method of claim 26, wherein deriving the second quantity from the first, the second, and the third signal comprises combining the first, the second, and the third signal to form a vector magnitude.

30. The method of claim 29, wherein comparing the second quantity to the second selected value comprises comparing the vector magnitude to the vector magnitude that would be produced in the second detection circuit by a magnetic field of 1700 gauss.

* * * * *